United States Patent [19]

Ikushima

[11] Patent Number: 5,540,945

[45] Date of Patent: Jul. 30, 1996

[54] PHARMACEUTICAL PREPARATIONS FOR ORAL ADMINISTRATION THAT ARE ADAPTED TO RELEASE THE DRUG AT APPROPRIATE SITES IN THE INTESTINES

[75] Inventor: Heiji Ikushima, Saitama-ken, Japan

[73] Assignee: Chugai Seiyaku Kabushiki Kaisha, Tokyo, Japan

[21] Appl. No.: 366,400

[22] Filed: Dec. 29, 1994

Related U.S. Application Data

[63] Continuation of Ser. No. 2,099, Jan. 8, 1993, abandoned, which is a continuation of Ser. No. 640,425, filed as PCT/JP90/00596, May. 10, 1990, abandoned.

[30] Foreign Application Priority Data

May 11, 1989 [JP] Japan .................. 1-116086

[51] Int. Cl.$^6$ .................. A61K 9/16; A61K 9/54
[52] U.S. Cl. .................. 424/490; 424/489; 424/493; 424/494; 424/496; 424/497; 424/458; 424/459; 424/461; 424/462
[58] Field of Search .................. 424/458, 459, 424/461, 462, 468, 470, 471, 472, 474, 493, 494, 495, 497, 489–492

[56] References Cited

U.S. PATENT DOCUMENTS

| | | | |
|---|---|---|---|
| 4,309,405 | 1/1982 | Guley et al. | 424/493 |
| 4,432,966 | 2/1984 | Zeitoun et al. | 424/471 X |
| 4,775,536 | 10/1988 | Patell | 424/471 |
| 4,800,084 | 1/1989 | Zerbe | 424/471 X |
| 4,808,416 | 2/1989 | Hata et al. | 424/494 X |
| 4,828,840 | 5/1989 | Sakamoto et al. | 424/474 |
| 4,871,549 | 10/1989 | Ueda et al. | 424/495 X |
| 4,874,613 | 10/1989 | Hsiao | 424/494 X |
| 4,968,508 | 11/1990 | Oren et al. | 424/468 |
| 4,971,805 | 11/1990 | Kitanishi et al. | 424/468 X |
| 5,026,559 | 6/1991 | Eichel | 424/474 |
| 5,026,560 | 6/1991 | Makino et al. | 424/468 X |

FOREIGN PATENT DOCUMENTS

| | | |
|---|---|---|
| 0247983 | 12/1987 | European Pat. Off. . |
| 0366621 | 5/1990 | European Pat. Off. . |
| 2066070 | 7/1981 | United Kingdom . |

*Primary Examiner*—Gollamudi S. Kishore
*Attorney, Agent, or Firm*—Marshall, O'Toole, Gerstein, Murray & Borun

[57] ABSTRACT

The improved pharmaceutical preparation for oral administration which is adapted to release the drug at appropriate sites in the intestines comprises: a core that comprises an active ingredient and a pharmaceutically acceptable excipient, a first layer that covers the core and which comprises an enteric or water-soluble ingredient and an optional insoluble ingredient, a second layer that covers the first layer and which comprises a non-enteric ingredient that dissolves upon reacting with at least one ingredient in the core, and a third layer that covers the second layer and which comprises an enteric ingredient. This preparation is characterized in that it will not release the active ingredient until after it reaches a desired site in the intestines and that, in addition, it is capable of controlling the rate at which the active ingredient is released after it has reached the desired site. Therefore, this preparation is particularly effective in administering active ingredients having absorption specificity at specific sites in the intestines or for treating diseases at specific sites in the intestines.

2 Claims, 5 Drawing Sheets

PHARMACEUTICAL PREPARATIONS FOR ORAL ADMINISTRATION THAT ARE ADAPTED TO RELEASE THE DRUG AT APPROPRIATE SITES IN THE INTESTINES

This is a Continuation of U.S. application Ser. No. 08/022, 099 filed on Jan. 8, 1993, now abandoned which is a continuation of U.S. application Ser. No. 07/640,425, filed as PCT/JP90/00596, May 10, 1990, now abandoned.

TECHNICAL FIELD

This invention relates to pharmaceutical preparations for oral administration that are adapted to release the drug at appropriate sites in the intestines. More particularly, this invention relates to the structure of a pharmaceutical preparation for oral administration that enables the drug to be released continuously at specific sites in the intestines.

BACKGROUND ART

Pharmaceutical preparations for oral administration are generally intended to have the drug disintegrated in the stomach, etc. to insure that its efficacy is exhibited as quickly as possible. Thus, little R&D efforts have so far been directed to pharmaceutical preparations for oral administration that are so adapted as to release the drug only at specific sites in the intestines. Even if L-ascorbic acid containing preparations are administered orally with a view to delivering the drug to the large intestine so that it is released there, the drug is decomposed in the stomach and mostly absorbed by the small intestine, with little being delivered to the large intestine.

Sustained-release preparations have been developed as pharmaceuticals that are administered once or twice a day and which yet are capable of maintaining the blood concentration of the drug beyond a certain level over a prolonged time. However, even such sustained-release preparations are incapable of permitting the drug to be released only at desired sites in the intestines. For instance, even if it is intended to have the drug absorbed by the large intestine, part of the drug will be released before it reaches the large intestine since it takes 4–5 hours for the administered drug to reach the large intestine during a fasting period. Further, the drug reaching the large intestine is released only slowly so that the percent absorption of the drug is too low to insure efficient administration of the drug. Besides sustained-release preparations, administration can be made through the rectum either in the form of suppositories or by means of enema but even these methods are incapable of delivering the drug effectively to every part of the large intestine. Hence, heretofore, no means have been available by which salazosulfapyridine and prednisolone which are therapeutics for ulcerous colitis can be efficiently administered to reach appropriate sites in the large intestine.

DISCLOSURE OF THE INVENTION

Under these circumstances, the present inventors conducted intensive studies in order to develop a pharmaceutical preparation for oral administration that would not release the drug until after it reached a desired site in the intestines and which, after reaching the desired site, would release all the drug within a desired period of time. As a result of these studies, the present invention has been accomplished.

The pharmaceutical preparation of the present invention which is to be administered orally and which is adapted to release the drug at appropriate sites in the intestines comprises:

(a) a core that comprises an active ingredient and a pharmaceutically acceptable excipient;

(b) a first layer that covers the core and which comprises an enteric ingredient;

(c) a second layer that covers the first layer and which comprises a non-enteric ingredient that dissolves upon reacting with at least one ingredient in the core; and (d) a third layer that covers the second layer and which comprises an enteric ingredient.

BEST MODE FOR CARRYING OUT THE INVENTION

The core of the pharmaceutical preparation of the present invention comprises an active ingredient and an excipient. The active ingredient can be selected from a broad range of efficacious substances that can be absorbed by the intestines and/or can be adhered to the intestinal walls, etc. Particularly, substances that are efficiently absorbed at a specific site such as the large intestine as well as therapeutics for diseases in the intestines can be used effectively.

The core may contain a disintegrator that accelerates the release of the active ingredient.

The core may further contain an additive material that dissolves the second layer. Such additive materials are not always necessary if the active ingredient dissolves the second layer. However, if the active ingredient has little or no dissolving power or if sufficient dissolving action cannot be exhibited even though the active ingredient has a strong dissolving power because it is present in a very small amount, additive materials will be used effectively. Additive materials are selected as appropriate in accordance with the component of the second layer. For instance, if a substance that is disintegratable in the stomach is used in the second layer, with a non-acidic substance such as indomethacin being used as the active ingredient, water-soluble acidic materials such as organic acids can be used as additive materials.

The third layer which forms the outermost shell of the pharmaceutical preparation of the present invention comprises an enteric substance. The third layer must be such that it prevents the inner layers from being destroyed in the stomach after the preparation is administered orally while it dissolves only after the preparation gets into the intestines. Hence, it is required that the third layer not decompose with gastric juice but can be dissolved with intestinal juice. Specific examples of materials that can be used to make the third layer include: synthetic high-molecular weight compounds such as cellulose acetate phthalate (CAP), cellulose propionate phthalate, cellulose acetate maleate, polyvinyl alcohol phthalate, styrene-acrylic acid copolymer, methyl acrylate-methacrylic acid copolymer, polyvinyl acetate phthalate, hydroxypropylmethyl cellulose phthalate (HPMCP), hydroxypropylmethyl cellulose acetate succinate (HPMCAS), methacrylic acid/methyl methacrylate copolymer, ethyl methacrylate-methyl methacrylate-chloro-trimethylammonium ethyl methacrylate copolymer, as well as those substances which can be used as enteric coating agents, as exemplified by the enteric ingredients listed below in connection with the description of the first layer.

The second layer comprises a non-enteric ingredient that dissolves upon reacting with at least one ingredient in the core. The second layer is provided in order to start the release of the active ingredient at a predetermined site in the intestines and to control the time over which it is released. The component of the second layer must be a non-enteric one that dissolves upon reaction with at least one ingredient in the core. Specific examples of such components include polyvinyl acetate diethyl aminoacetate (AEA), polyvinyl aminoacetal, and dimethylaminoethyl methacrylate-methyl methacrylate copolymer. Among these, substances that dissolve in an acidic region (pH 1–5) but which will not dissolve in a neutral or alkaline region are preferably used.

The first layer comprises an enteric or water-soluble ingredient. The first layer is present in order to insulate the core from the second layer, thereby controlling the time at which the active ingredient starts to be released. Specific examples of the component of the first layer include: enteric ingredients such as hydroxypropylmethyl cellulose phthalate (HPMCP), hydroxypropylmethyl cellulose acetate succinate (HPMCAS), methacrylic acid-methyl methacrylate copolymer, ethyl methacrylate-methyl methacrylate-chlorotrimethylammonium ethyl methacrylate copolymer, cellulose acetate phthalate (CAP), cellulose propionate phthalate, cellulose acetate maleate, polyvinyl acetate phthalate, polyvinyl alcohol phthalate, styrene-acrylic acid copolymer, and methyl acrylate-methacrylic acid copolymer; and water-soluble ingredients such as cellulosic derivatives (e.g. acetyl cellulose, methyl cellulose, hydroxypropyl cellulose, hydroxypropylmethyl cellulose and carboxymethyl cellulose sodium) and natural high-molecular weight compounds (e.g. gelatin). The release start time can be delayed by adding insoluble ingredients such as ethyl cellulose (E.C). Such insoluble ingredients can be added in amounts ranging from 0 to 50% of the first layer.

Each of the first, second and third layers may have plasticizers, antistats and other compounds incorporated therein for the purpose of improving coating and film-forming properties.

When it enters the intestines, the pharmaceutical preparation of the present invention first has the third layer dissolved by intestinal juice. Since the second layer is non-enteric, intestinal juice will infiltrate the preparation without dissolving the second layer. When the intestinal juice reaches the first layer, infiltration into the first layer or dissolution of this layer itself will start. When the infiltration into or dissolution of the first layer causes the core to contact the solution, the ingredients of the core will diffuse through the solution. Upon contact with the additive material and/or active ingredient in the core, the second layer starts to dissolve, eventually causing the active ingredient to be released into the intestines.

A specific structure of the preparation of the present invention is designed in such a way that the active ingredient can be released at a desired site in the intestines in accordance with the above-described mechanism of release. For example, the time required for intestinal juice to reach the first layer or the time required for dissolution by the additive materials, etc. can be controlled by varying the thickness of the second layer. Further, the release rate of the active ingredient can also be controlled by selecting proper combinations of the additive materials and the second layer which is to be dissolved by them or by changing the component in the second layer. It should be noted here that the second layer is required to have such a strength as to prevent it from being destroyed before it is dissolved by the active ingredient or additive materials.

The individual layers in the preparation of the present invention are usually coated in the following amounts. In the case of granules, the first layer is coated in an amount of 5–60 wt % of the core, the second layer is coated in an amount of 10–80 wt % of the core with the first layer, and the third layer is coated in an amount of 10–30 wt % of the core with the first and second layers. In the case of tablets or capsules, the first, second and third layers are usually coated in the respective amounts of 0.5–10%, 0.5–10% and 1–10%, on the basis of the bore tablet or capsule weight. As already described above, the coating weights of the respective layers can be appropriately selected in order to obtain pharmaceutical preparations for oral administration that are adapted to release the drug at desired sites in the intestines.

Figure 1:
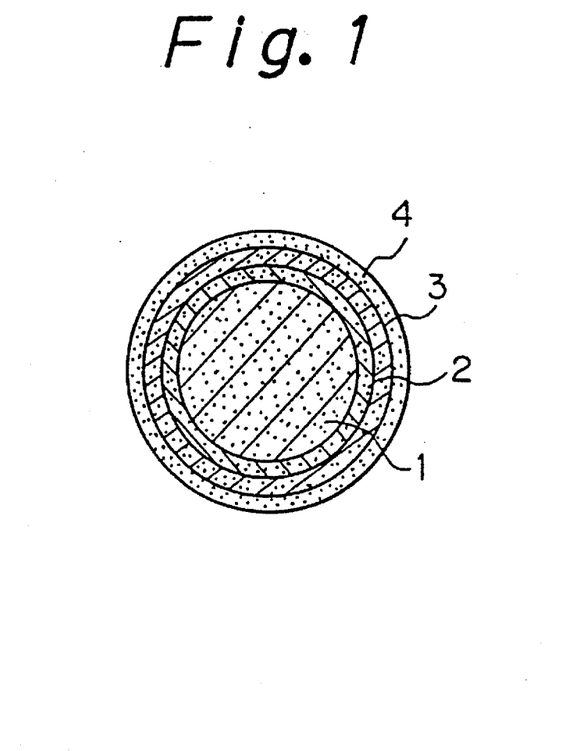
FIG. 1 shows an example of the structure of a granule according to the present invention.
Figure 2:
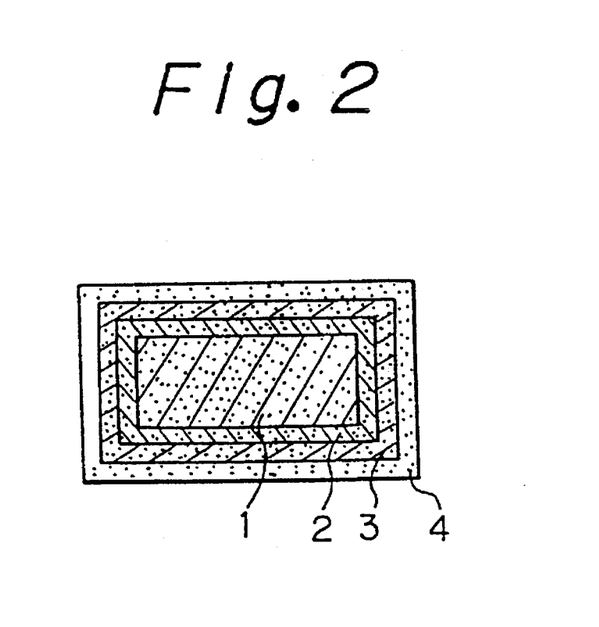
FIG. 2 shows an example of the structure of a tablet according to the present invention.
Figure 3A:
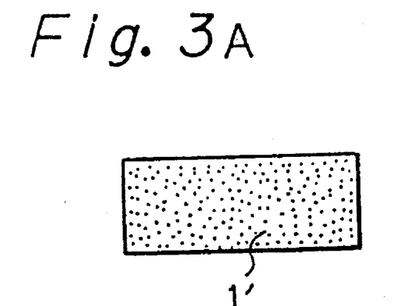
FIG. 3 shows various types (A to E) of the core in the pharmaceutical preparation of the present invention.
Figure 3B:
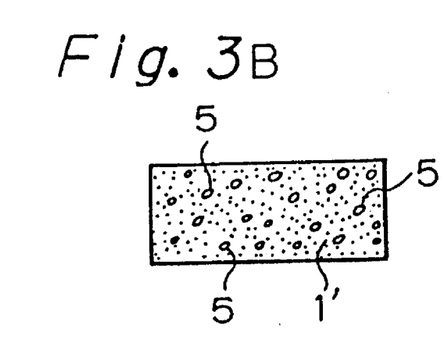
Figure 3C:
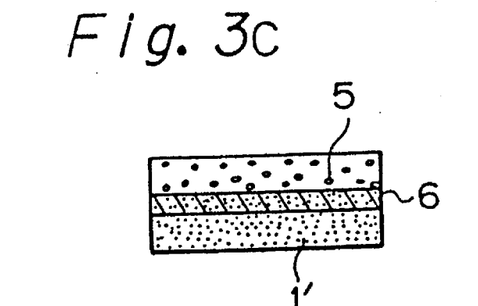
Figure 3D:
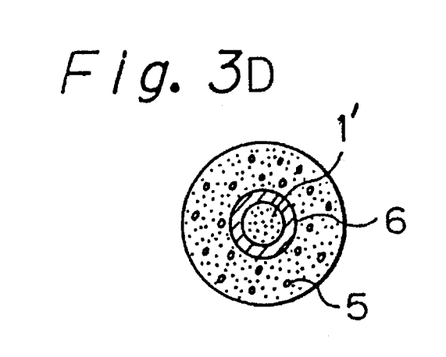
Figure 3E:
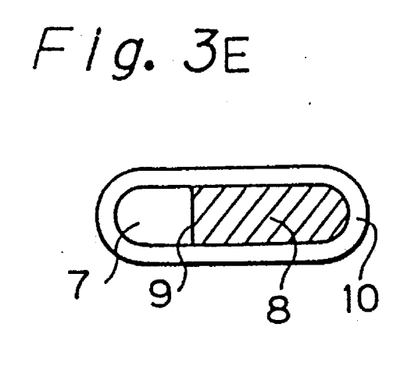

The structure of the core is not limited in any particular way as long as it is capable of releasing the active ingredient by the mechanism described above. Specific examples of the core structure are listed below: a structure that solely consists of the active ingredient and an excipient in the absence of any additive material; a structure in which the active ingredient and an additive material are present uniformly (FIG. 3A); a structure in which a predetermined amount of additive material is mixed within the active ingredient (FIG. 3B); a structure having the active ingredient and an additive material present in different layers, a structure having an isolating layer between a layer made of the active ingredient and a layer made of an additive material (FIGS. 3C and 3D); and a structure having the active ingredient placed within a capsule (FIG. 3E). When additive materials are to be used, factors such as their reactivity with the active ingredient have to be taken into account. Particularly in the case where additive materials are acidic whereas the active ingredient is not acidic, the structure shown in FIG. 3B, C, D, or E is preferably employed.

The process for producing the pharmaceutical preparation of the present invention is not limited in any particular way and customary methods known to one skilled in the art can be employed. For example, the core can be coated with various apparatus equipped with conventionally known pan coaters, fluidized coaters and a forced-air drying mechanism. Coating solutions are also not limited in any particular way and various ingredients can be used, such as plasticizers, surfactants, higher alcohols, higher aliphatic acid esters of glycerin for improving the film-forming property, additives for adjusting water permeability, water vapor permeability and light transmission (e.g., stearic acid, polyethylene glycol, talc and titanium oxide), antistats that are added for the purpose of improving the efficiency of coating operations (e.g., stearic acid and polyethylene glycols), silicone resins for defoaming purposes, dyes and inorganic pigments for coloring purposes, and flavoring agents.

The pharmaceutical preparation of the present invention is chiefly characterized in that the active ingredient will not be released until after it reaches a desired site in the intestines and that the release rate of the active ingredient can be controlled after reaching the desired site. Hence, the pharmaceutical preparation of the present invention can be used with particular effectiveness not only in administering active ingredients that have absorption specificity at specific sites in the intestines such as in the large intestine but also for treating diseases at specific sites in the intestines. This has the potential to allow heretofore impossible or difficult drug administrations and disease treatments to be accomplished effectively. For example, the pharmaceutical preparation of the present invention will prove extremely effective as a means of effective administration of reducing agents for the purpose of preventing not only the occurrence of polyp in the large intestine due to a significantly oxidizing environment but also the development of such polyp into adenoma or cancer.

The following examples are provided for the purpose of further illustrating the present invention in a more specific and detailed manner but it should be understood that the scope of the present invention is only determined by the claims and that it is in no way limited by those examples.

In the following, all "parts" are on a weight basis.

EXAMPLE 1

Granules as a Preparation for Delivering
L-Ascorbic Acid to the Large Intestine

L-ascorbic acid (72 parts), crystalline cellulose (15 parts), lactose (5 parts), stearic acid (5 parts) and a 50% ethanol aqueous solution containing 10 wt % hydroxypropyl cellulose were kneaded in such a way that the content of hydroxypropyl cellulose would be equivalent to 3 parts as solids. The mixture was charged into a cylindrical granulator equipped with a 0.8 mm$^\phi$ net, where granulation and drying were effected.

The dry granules obtained (300 parts) were coated in the usual manner using a coating solution consisting of hydroxypropylmethyl cellulose phthalate (HP-55, 7 parts), purified shellac (0.7 parts), acetylated monoglyceride (0.7 parts), methylene chloride (45.8 parts) and ethanol (45.8 parts) in such a way that the solids content would be equivalent to 75 parts, whereby the granules were coated with a first layer.

The granules with the first layer (300 parts) were coated in the usual manner using a coating solution for a second layer that consisted of AEA (5 parts), polyethylene glycol (2 parts), ethanol (40 parts) and methylene chloride (53 parts) in such a way that the solids content would be equivalent to 60 parts, whereby the granules were further coated with a second layer.

The granules with the first and second layers (300 parts) were coated using a coating solution of the same composition as the first layer in such a way that the solids content would be 60 parts, whereby granules were obtained as a preparation for delivering L-ascorbic acid to the large intestine.

EXAMPLE 2

The bare granules (300 parts) prepared in Example 1 were coated in the usual manner using a coating solution consisting of hydroxypropylmethyl cellulose acetate succinate (HPMCAS, 10 parts), triethyl citrate (4 parts) and pure water (86 parts) in such a way that the solids content would be equivalent to 60 parts, whereby the granules were coated with a first layer. Coating of a second and a third layer was accomplished as in Example 1.

EXAMPLE 3

A first layer was applied in the usual manner using a coating solution consisting of hydroxypropylmethyl cellulose acetate succinate (HPMCAS, 10 parts), triethyl citrate (4 parts) and pure water (86 parts) in such a way that the solids content would be equivalent to 90 parts. Subsequently, coating of a second and a third layer was accomplished as in Example 1.

EXAMPLE 4

Granules as a Preparation for Delivering
Indomethacin to the Large Intestine

Indomethacin (10 parts), lactose (50 parts), citric acid (20 parts), crystalline cellulose (15 parts) and hydroxypropyl cellulose (5 parts) were mixed and kneaded in the presence of water. The mixture was granulated and dried in a cylindrical granulator equipped with a 0.8 mm$^\phi$ net.

The dry granules (300 parts) obtained were coated with a first, a second and a third layer as in Example 3, whereby a preparation for delivering indomethacin to the large intestine was obtained.

EXAMPLE 5

Granules as a Preparation for Delivering
Salazosulfapyridine to the Large Intestine Salazosulfapyridine (50 parts), low-substitution hydroxypropyl cellulose (10 parts), tartaric acid (20 parts), crystalline cellulose (5 parts), corn starch (10 parts) and hydroxypropyl cellulose (5 parts) were mixed and kneaded in the presence of water. Then, the mixture was granulated and dried in a cylindrical granulator equipped with a 1.0 mm$^\phi$ net.

The dried granules (300 parts) obtained were coated with a first, a second and a third layer as in Example 3, whereby a preparation for delivering salazosulfapyridine to the large intestine was obtained.

EXAMPLE 6

Tablet as a Preparation for Delivering Prednisolone
to the Large Intestine

Prednisolone (25 parts), lactose (25 parts), crystalline cellulose (20 parts), low-substitution hydroxypropyl cellulose (25 parts) and hydroxypropyl cellulose (5 parts) were mixed and then kneaded in the presence of water. Granules were produced by treatment with a speed mill and the resulting granules were dried. The dried product (99 parts) was mixed with magnesium stearate (1 part) and tablets each weighing 200 mg were prepared in the usual manner. The tablets (300 parts) were coated with a first layer in the usual manner using a coating solution consisting of hydroxypropylmethyl cellulose phthalate (HP-55, 7 parts), purified shellac (0.7 parts), acetylated monoglyceride (0.7 parts), methylene chloride (45.8 parts) and ethanol (45.8 parts) in such a way that the solids content would be equivalent to 7.5 parts.

The tablets with the first layer (300 parts) were coated with a second layer using a dimethylaminoethyl methacrylate-methyl methacrylate copolymer (Eudragit E.30D) as a coating solution in such a way that the solids content would be equivalent to 6.0 parts.

The tablets with the first and second layers (300 parts) were then coated with a third layer using a methyl methacrylate-methacrylic acid copolymer (Eudragit L-30D 55) as a coating solution in such a way that the solids content would be equivalent to 6.0 parts.

EXAMPLE 7

Tablet as a Preparation for Delivering Prednisolone to the Large Intestine

Tablets were prepared by repeating the same procedure as in Example 6 except that 25 parts of prednisolone was replaced by 10 parts of prednisolone and 15 parts of citric acid.

EXAMPLE 8

Tablet as a System for Delivering Prednisolone to the Large Intestine

To 92.7 parts of L-ascorbic acid, an ethanol suspension containing 5 wt % of hydroxypropyl cellulose and 30 wt % of talc was added in such a way as to provide a solids content equivalent to 7.3 parts. The ingredients were kneaded, granulated with a milling granulator and dried to obtain granules for tablet.

Sixty-five parts of the resulting granules were mixed with 24.5 parts of crystalline cellulose, 10 parts of low-substitution hydroxypropyl cellulose and 0.5 parts of magnesium stearate and tablets each weighing 165 mg were produced in the usual manner.

The tablets (400 parts) were coated with a first layer in the usual manner using a coating solution consisting of hydroxypropylmethyl cellulose phthalate (HPMCP:HP-55, 3 parts), polyethylene glycol (PEG-6000, 0.6 parts) ethanol (40 parts) and methylene chloride (56.4 parts) in such a way that the solids content would be equivalent to 3.5 wt %. The tablets with the first layer (400 parts) were coated with a second layer in the usual manner using a coating solution consisting of polyvinyl acetate diethyl aminoacetate (AEA, 3 parts), talc (3 parts), PEG-6000 (0.6 parts), stearic acid (0.6 parts), ethanol (40 parts) and methylene chloride (52.8 parts) in such a way that the solids content would be equivalent to 2 wt %.

The same procedure was repeated to prepare two-layer coated tablets except that the solids content in the second layer was changed to 4 wt % or 6 wt %.

Each of the three kinds of two-layer coated tablets (400 parts) were coated with an additional layer in the usual manner using a coating solution consisting of HP-55 (3 parts), PEG-6000 (0.6 parts), stearic acid (0.6 parts), ethanol (40 parts) and methylene chloride (55.8 parts) in such a way that the solids content would be equivalent to 6 wt %, whereby a system for delivering L-ascorbic acid to the large intestine was obtained.

EXAMPLE 9

Tablet as a system for Delivering Salazosulfapyridine to the Large Intestine

Salazosulfapyridine (30 parts), tartaric acid (20 parts), crystalline cellulose (20 parts), lactose (24.5 parts), low-substitution hydroxypropyl cellulose (LH-31, 5 parts) and magnesium stearate (0.5 parts) were mixed and tablets each weighing 200 mg were prepared in the usual manner. These tablets (400 parts) were coated with a first layer in the usual manner using a coating solution consisting of HPMCP (HP-55, 2.75 parts), hydroxypropylmethyl cellulose (HPMC:TC-5, 0.25 parts), PEG-6000 (0.6 parts), ethanol (40 parts) and methylene chloride (56.4 parts) in such a way that the solids content would be equivalent to 4.5 wt %.

The tablets were then coated with a second and third layer as in Example 8, whereby a system for delivering salazosulfapyridine to the large intestine was obtained.

EXAMPLE 10

Capsule as a Preparation for Oral Administration of Erythropoietin

A solution (150 mg) of middle-chain aliphatic acid triglyceride (MCT) containing 0.01% erythropoietin was filled into hard gelatin capsules (No. 4) and a cap was sealed to the body, thereby obtaining capsules filled with erythropoietin in liquid form (which are hereinafter referred to as "capsules").

The capsules (400 g) were charged into a centrifugal granulator. While they were sprayed with an 80% ethanol solution containing 5 wt % of HPC-L under rotation, a powder mixture of crystalline cellulose (50 parts) and citric acid (50 parts) was added in an amount of 20 wt % of the capsule weight so that it was coated onto the capsule surface. Upon drying, capsules having the structure shown in FIG. 3E were obtained.

Using the resulting acid-coated capsules, the procedure of Example 9 was repeated to obtain a system for delivering erythropoietin to appropriate sites in the intestines.

EXAMPLE 11

Capsule as a Preparation for Oral Administration of rG-CSF

A solution (150 mg) of MCT containing 0.1% rG-CSF was filled into hard gelatin capsules (No. 4) and a cap was sealed to the body, thereby obtaining capsules filled with rG-CSF in liquid form.

By repeating the same procedure as in Example 10, a system for delivering rG-CSF to appropriate sites in the intestines was obtained.

Experiment 1

Granules A, B and C prepared in Example 1, 2, and 3, respectively, were subjected to a dissolution test by the second method of dissolution test (paddle method) described in the Eleventh Revised Edition of the Japanese Pharmacopoeia. The test was conducted using 900 ml of test solutions at a temperature of 37°±0.5° C. with the paddle being rotated at 100 rpm. The sample weight was 1.0 g. The test solutions were sampled at given time intervals and the amount of L-ascorbic acid in the test solutions was determined to calculate the percent dissolution. As the test solutions, JP Solutions I and II having the following formulas were used.

JP Solution I: 2.0 g of sodium chloride dissolved in 24.0 ml of dilute hydrochloric acid and water is added to make 1,000 ml.

JP Solution II: 250 ml of a 0.2M potassium dihydrogenphosphate is mixed with 118 ml of a 0.2M sodium hydroxide test solution and water is added to make 1,000 ml.

Figure 4:
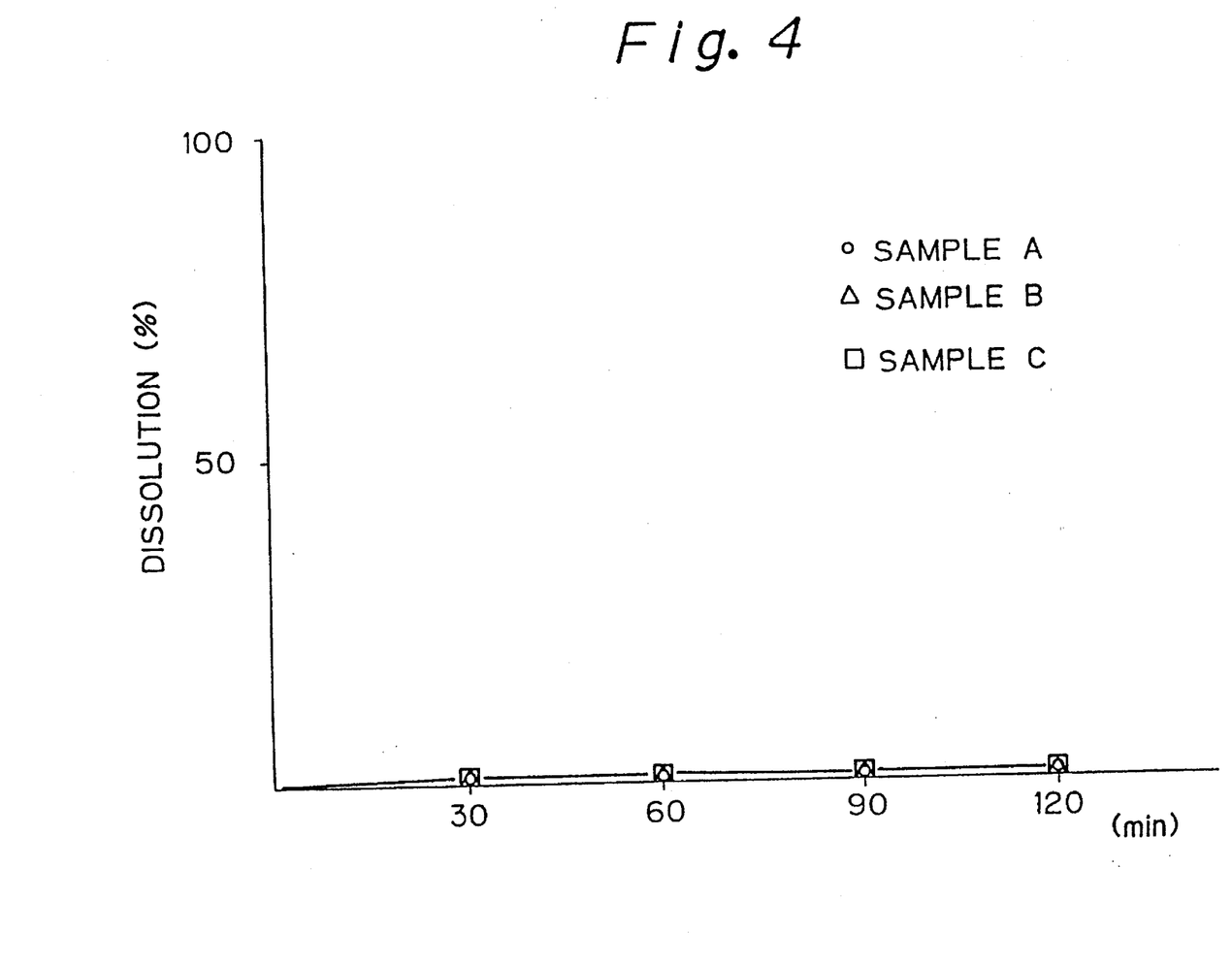
FIGS. 4, 5 and 6 are each a graph showing the results of a dissolution test in terms of the relationship between dissolution time and percent dissolution.
Figure 5:
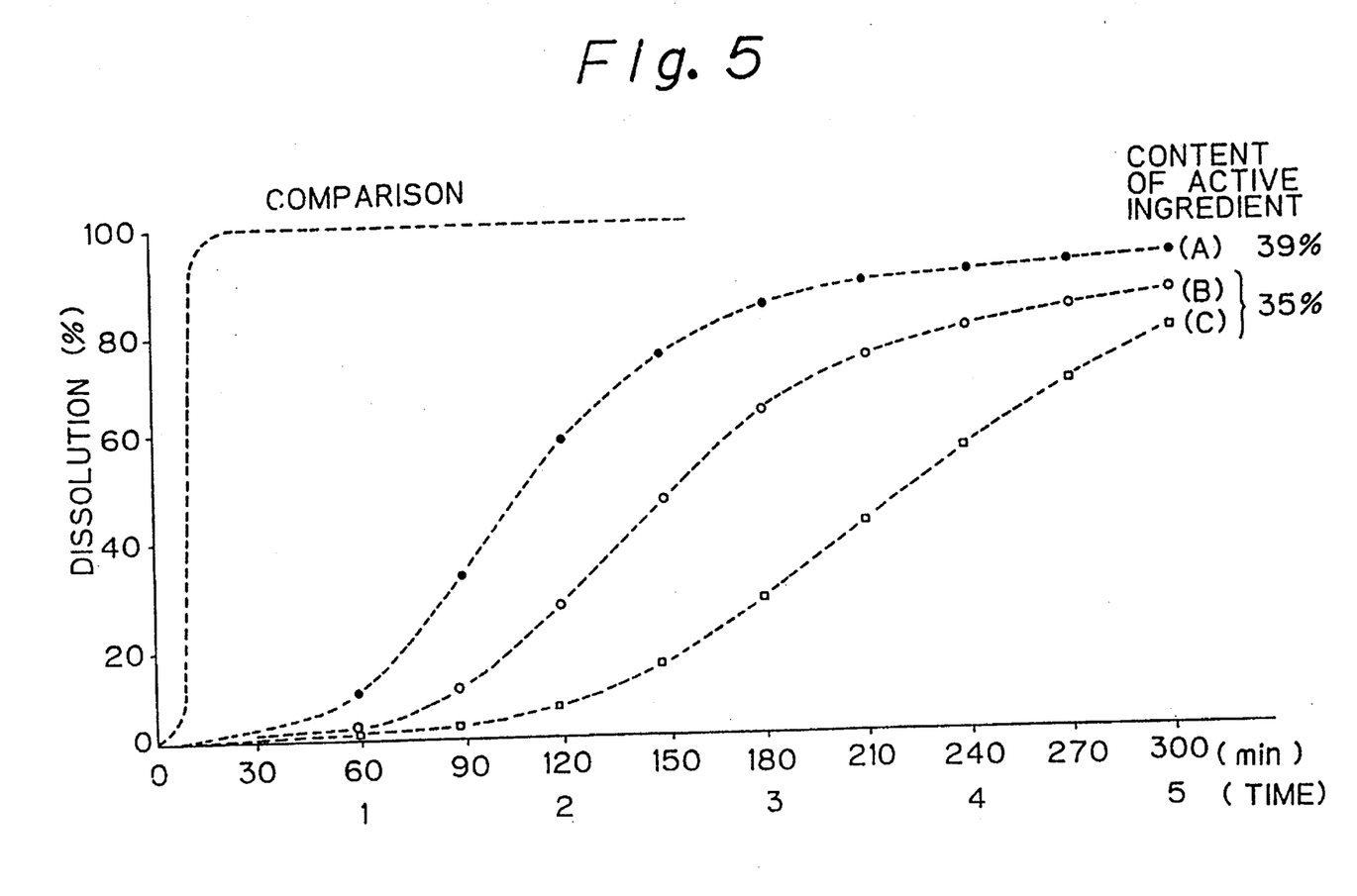

The test results are shown in Table 1, as well as in FIGS. 4 and 5. As a comparison, granules were prepared with a first layer coated as in Example 1. In Table 1 and FIGS. 4 and 5, (A) refers to Example 1, (B) to Example 2, and (C) to Example 3.

TABLE 1

| Sample | Dissolution in 2 hours | 50% Dissolution time | 80% Dissolution time | Lag time |
|---|---|---|---|---|
| A | 60% | 100 min. | 160 min. | 45 min. |
| B | 25% | 155 min. | 240 min. | 75 min. |
| C | 6.5% | 255 min. | 300 min. | 2 hours |
| Comparison | 100% | 15 min. | 20 min. | 5 min. |

Experiment 2

Figure 6:
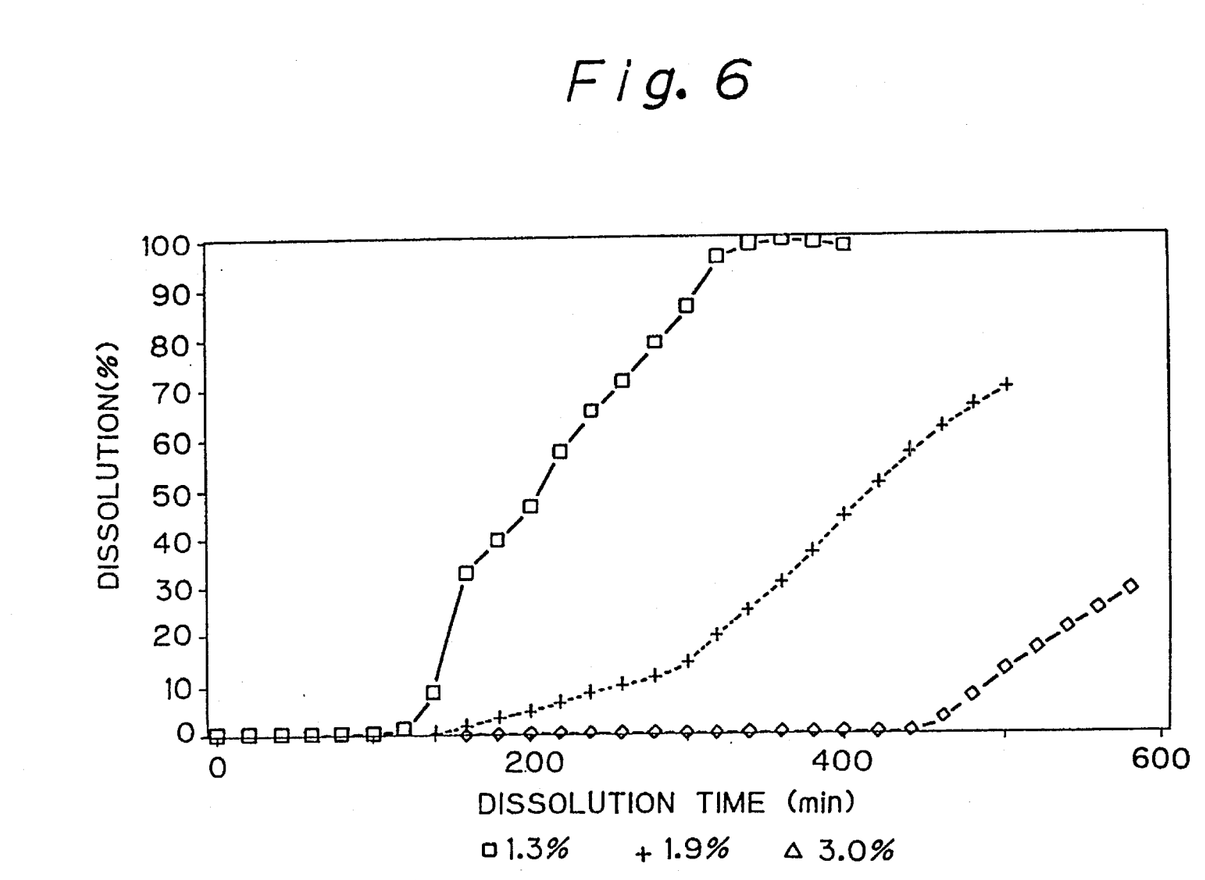

Samples 1, 2, 3 which were the three kinds of tablets prepared by Example 8 were subjected to the same dissolution test as in Experiment 1. The results are shown in FIG. 6 (average for n=6).

I claim:

1. A pharmaceutical preparation for oral administration which is a granule and is adapted to release the drug at appropriate sites in the intestines, said preparation consisting of;

(a) a core that comprises erythropoietin or granulocyte colony-stimulating factor as the active ingredient and a pharmaceutically acceptable excipient;

(b) a first layer surrounding the core and which comprises an enteric ingredient consisting of hydroxypropylmethyl cellulose phthalate, hydroxypropylmethyl cellulose acetate succinate, methacrylic acid-methyl methacrylate copolymer, ethyl methacrylate-methyl methacrylate-chloro-trimethylammonium ethyl methacrylate copolymer, cellulose acetate phthalate, cellulose propionate phthalate, cellulose acetate maleate, polyvinyl acetate phthalate, polyvinyl alcohol phthalate, styrene-acrylic acid copolymer, methyl acrylate-methacrylic acid copolymer, or a water-soluble ingredient consisting of acetyl cellulose, methyl cellulose, hydroxypropyl cellulose, hydroxypropylmethyl cellulose, or carboxymethyl cellulose sodium, said first layer being present in an amount of about 5–60 weight percent of the core;

(c) a second layer which is an enteric layer surrounding the first layer and which comprises a non-enteric ingredient, said layer is permeable to intestinal fluid and dissolves upon reacting with intestinal fluid combined with at least one ingredient in the core, said non-enteric ingredient of the second layer comprising polyvinyl acetate dimethyl aminoacetate, polyvinyl aminoacetal, or dimethylaminoethyl methacrylate-methyl methacrylate copolymer and, said second layer being present in an amount of about 10–30 weight percent of the core and first layer; and (d) a third layer surrounding the second layer and which comprises an enteric ingredient, said third layer consisting cellulose acetate phthalate, cellulose propionate phthalate, cellulose acetate maleate, polyvinyl alcohol phthalate, styrene-acrylic acid copolymer, methyl acrylate-methacrylic acid copolymer, polyvinyl acetate phthalate, hydroxypropylmethyl cellulose phthalate, hydroxypropylmethyl cellulose acetate succinate, methacrylic acid/methyl methacrylate copolymer, or ethyl methacrylate-methyl methacrylate-chloro-trimethylammonium ethyl methacrylate copolymer; said third layer being present in an amount of about 10–30 weight percent of the core, first layer and second layer.

2. A pharmaceutical preparation for oral administration which is a tablet or capsule and is adapted to release the drug at appropriate sites in the intestines, said preparation consisting of;

(a) a core that comprises erythropoietin or granulocyte colony-stimulating factor as the active ingredient and a pharmaceutically acceptable excipient;

(b) a first layer surrounding the core and which comprises an enteric ingredient consisting of hydroxypropylmethyl cellulose phthalate, hydroxypropylmethyl cellulose acetate succinate, methacrylic acid-methyl methacrylate copolymer, ethyl methacrylate-methyl methacrylate-chloro-trimethylammonium ethyl methacrylate copolymer, cellulose acetate phthalate, cellulose propionate phthalate, cellulose acetate maleate, polyvinyl acetate phthalate, polyvinyl alcohol phthalate, styrene-acrylic acid copolymer, methyl acrylate-methacrylic acid copolymer, or a water-soluble ingredient consisting of acetyl cellulose, methyl cellulose, hydroxypropyl cellulose, hydroxypropylmethyl cellulose, or carboxymethyl cellulose sodium; said first layer being present in an amount of about 0.5–10 weight percent of the core;

(c) a second layer which is an enteric layer surrounding the first layer and which comprises a non-enteric ingredient, said layer is permeable to intestinal fluid and that dissolves upon reacting with intestinal fluid combined with at least one ingredient in the core, said non-enteric ingredient of the second layer comprising polyvinyl acetate diethyl aminoacetate, polyvinyl aminoacetal, or dimethylaminoethyl methacrylate-methyl methacrylate copolymer and; said second layer being present in an mount of about 0.5–10 amount weight percent of the core and first layer and (d) a third layer surrounding the second layer and which comprises an enteric ingredient, said third layer consisting cellulose acetate phthalate, cellulose propionate phthalate, cellulose acetate maleate, polyvinyl alcohol phthalate, styrene-acrylic acid copolymer, methyl acrylate-methacrylic acid copolymer, polyvinyl acetate phthalate, hydroxypropylmethyl cellulose phthalate, hydroxypropylmethyl cellulose acetate succinate, methacrylic acid/methyl methacrylate copolymer, or ethyl methacrylate-methyl methacrylate-chloro-trimethylammonium ethyl methacrylate copolymer and, said third layer being present in an mount of about 1.0–10 weight percent of the core, first layer and second layer.

* * * * *

UNITED STATES PATENT AND TRADEMARK OFFICE
CERTIFICATE OF CORRECTION

PATENT NO. : 5,540,945
DATED : July 30, 1996
INVENTOR(S) : Heiji Ikushima

It is certified that error appears in the above-identified patent and that said Letters Patent is hereby corrected as shown below:

Column 4, line 16, "10-80 wt%" should be -- 10-30 wt% --.

Column 10, line 43, "mount" should be --amount--.

Signed and Sealed this

Thirty-first Day of December, 1996

Attest:

BRUCE LEHMAN

Attesting Officer     Commissioner of Patents and Trademarks